(12) United States Patent
Tunnermann et al.

(10) Patent No.: US 8,083,731 B2
(45) Date of Patent: Dec. 27, 2011

(54) APPARATUS AND METHOD FOR LASER TREATMENT OF A BIOLOGICAL MATERIAL

(75) Inventors: Andreas Tunnermann, Weimar (DE); Klaus Vogler, Eckental (DE)

(73) Assignees: Wavelight AG, Erlangen (DE); Fraunhofer-Gesellschaft zur Forderung der Angewandten Forshung E.V., Munich (DE)

( * ) Notice: Subject to any disclaimer, the term of this patent is extended or adjusted under 35 U.S.C. 154(b) by 1273 days.

(21) Appl. No.: 11/681,612

(22) Filed: Mar. 2, 2007

(65) Prior Publication Data

US 2008/0015662 A1    Jan. 17, 2008

(30) Foreign Application Priority Data

Mar. 3, 2006   (EP) .................................... 06004388

(51) Int. Cl.
*A61B 18/20* (2006.01)
(52) U.S. Cl. .................... 606/3; 606/4; 606/10; 607/88; 607/89
(58) Field of Classification Search .................. 606/3–6, 606/8–18; 607/88–91; 128/898
See application file for complete search history.

(56) References Cited

U.S. PATENT DOCUMENTS

| | | | |
|---|---|---|---|
| 6,610,052 B2 * | 8/2003 | Furumoto | 606/9 |
| 7,131,968 B2 * | 11/2006 | Bendett et al. | 606/10 |
| 2003/0222324 A1 | 12/2003 | Sun et al. | |
| 2004/0199150 A1 * | 10/2004 | Lai | 606/5 |
| 2005/0015120 A1 | 1/2005 | Seibel et al. | |
| 2005/0236380 A1 | 10/2005 | Tsuno et al. | |

FOREIGN PATENT DOCUMENTS

| | | |
|---|---|---|
| DE | 10125206 B4 | 3/2005 |
| WO | 02/074176 | 9/2002 |

OTHER PUBLICATIONS

Tibor, Juhasz, et al., "Corneal Refractive Surgery with Femtosecond Lasers," IEEE Journal of Selected Topics in Quantum Electronics, vol. 5, No. 4, pp. 902-910 (Jul./Aug. 1999).
Arnold, C.L., et al., "Streak Formation as Side Effect of Optical Breakdown During Processing the Bulk of Transparent Kerr Media with Ultra-Short Laser Pulses," Appl. Phys. B, vol. 80, pp. 247-253 (2005).

* cited by examiner

*Primary Examiner* — Ahmed Farah
(74) *Attorney, Agent, or Firm* — Haynes and Boone, LLP

(57) ABSTRACT

An apparatus for laser processing of a material, in particular the eye cornea, emits on to the material a train (18') of laser radiation pulses having a pulse duration in the femtosecond range. The pulse train comprises a multiplicity of successive pulse groups, each pulse group comprising at least two laser radiation pulses (20', 22'). The pulses of a pulse group are directed at substantially the same processing site of the material, but the pulses of successive groups are directed at substantially different processing sites of the material. According to the invention the time interval between successive laser radiation pulses of a pulse group is in the nanosecond range. In particular, the intensity or energy of the pulses within a pulse group is graduated, in such a way that a preceding prepulse (20') has substantially lower intensity or energy than a following main pulse (22').

17 Claims, 2 Drawing Sheets

APPARATUS AND METHOD FOR LASER TREATMENT OF A BIOLOGICAL MATERIAL

The invention relates to an apparatus and a method for laser processing of a biological material.

In principle, the invention is not restricted to specific materials. Application of the invention to both inorganic and organic materials is conceivable. However, a preferred application of the invention is in the processing of biological materials, in particular for surgical purposes. Possible biological materials are, for example, the cornea, but also other parts of the human or animal body, in particular other parts of the eye. The following exposition of the invention is given with a view especially to the laser-surgical processing of the cornea with the aim of correcting vision defects, although it must be emphasised that the invention can equally be used with other materials and for other application purposes, whether on the living body or on inanimate matter.

The use of femtosecond lasers for material processing is known. A femtosecond laser supplies pulsed laser radiation with ultra-short pulse durations in the femtosecond range. In the context of the invention, the term "femtosecond range" should be understood to mean that it also includes, in particular, pulse lengths in the high three-digit femtosecond range, even up to single-digit picoseconds. Regarding the term "pulse duration" or "pulse length", this relates to a statistical mean value, since it is self-evident that the individual pulses of the laser generally are not all of exactly equal length or have an exactly equal intensity curve. For example, the half-value length of a laser radiation pulse may be specified as its pulse duration.

Commercially available femtosecond lasers for material processing include a laser oscillator which can generate femtosecond pulses with a repetition rate or pulse sequence frequency in the MHz range, for example, of the order of magnitude of 1 MHz to 100 MHz, and with a comparatively low pulse energy in the lower nJ range, for example from 0.1 to 10 nJ. The pulse repetition range in the MHz range corresponds to a time interval between successive pulses of the laser oscillator in the nanosecond range.

To amplify the generally relatively low-energy pulses of conventional fs laser oscillators, it is known, according to a procedure referred to as "chirped pulse amplification" (CPA) in specialist circles, initially to stretch the pulses temporally, optionally after pre-amplification, before they are amplified at a comparatively low intensity level. The pulses are then re-compressed temporally. In this way very energy-rich yet extremely short laser radiation pulses can be generated. The energy of the pulses thus generated is, for example, in the µJ or even the mJ range. They are extremely well-suited to the precise, non-thermal microprocessing of materials, for which reason femtosecond lasers are also used for applications in medicine, in particular ophthalmology.

For example, in various procedures of eye surgery it is necessary to separate tissue structures in or on the eye. For example, in refractive eye surgery, which seeks to correct vision defects by changing the refractive properties of the cornea, incisions must be made in the cornea in some procedures, for example, in LASIK (laser keratomileusis), in which a flap still connected to the cornea is separated from a portion of the edge of the corneal epithelium, which flap can be folded aside in order to expose the corneal regions located below it. In a variant of LASIK, after the flap has been folded away, photo-ablation of the exposed regions of the stroma is carried out by irradiation with pulsed laser radiation in the lower UV wavelength range according to an ablation profile prepared for the particular patient. In another LASIK variant a small lens-like slice is first cut free within the cornea by means of irradiated fs pulses before the flap is produced. This lens slice corresponds to the volume of material to be removed from the cornea to correct the vision defect. After the flap has been folded away the severed lens slice can be removed and the flap folded back again. Moreover, the use of femtosecond lasers in refractive eye surgery is considered not only for making incisions, but also for multi-layer intrastromal material vaporisation which does not require corneal incisions.

Regarding the state of the art in the application of femtosecond lasers in refractive eye surgery, reference is made to the following two publications as examples:

Tibor Juhasz et al., "Corneal Refractive Surgery with Femtosecond Lasers", IEEE Journal of Selected Topics in Quantum Electronics, Vol. 5, No. 4, July/August 1999, pp. 902-910

C. L. Arnold et al., "Streak formation as side effect of optical breakdown during processing the bulk of transparent Kerr media with ultra-short laser pulses", Applied Physics B 80, 2005, pp. 247-253

At least in refractive femtosecond eye surgery, it has been usual up to now to effect the desired separation or removal of tissue with a train of individual fs pulses repeated at equal time intervals, the pulse repetition rate of the pulse train irradiated into the eye being typically from a few kHz to a few hundred kHz, depending on the efficiency of the main amplifier of the femtosecond laser (a regenerative amplifier is often used). The laser beam is guided over the area of tissue to be processed in such a way that two successive individual pulses do not impinge on the same site of the tissue, but on adjacent sites, although under some circumstances they may overlap somewhat.

DE 101 25 206 B4 proposes the use of double pulses instead of single pulses for the microstructuring of materials such as quartz glass and graphite by means of fs laser pulses, the double pulses being composed of a lower-energy prepulse and a following higher-energy main pulse. According to this document the energy of the prepulse and of the main pulse is in each case below the microstructuring threshold of the material to be processed. Only the energy of both partial pulses together is above this threshold. It is claimed that the prepulse excites primary processes in the material which are then still more perceptible upon impingement of the main pulse. It is claimed that the material can thereby be better processed by the main pulse, without causing fissures or stresses in the material.

So that change brought about in the material by the prepulse is made more perceptible upon impingement of the main pulse, the time interval between the main pulse and the prepulse is claimed to lie on a sub-picosecond or a picosecond timescale. In concrete terms, a time interval of 0.6 ps is stated for quartz glass and of 2 ps for graphite. There is no mention in the document of how the double pulses are generated, and in particular of how the extremely short time interval between prepulse and main pulse can be achieved stably and reliably.

It is the object of the invention to specify a way in which, in the laser processing of a material, in particular a biological material, high-quality results can be achieved whereby undesired material changes outside the material zones to be processed can be very effectively avoided. These high-quality results are to be reliably achievable, that is, reproducible with relatively high uniformity, which is of enormous importance especially in the case of laser treatments of the eye or other sensitive parts of the body.

In achieving this object, the invention starts from an apparatus for laser processing of a biological material, the apparatus being arranged to emit in the direction of the material a train of laser radiation pulses having a pulse duration in the femtosecond range, the pulse train comprising a multiplicity of successive pulse groups, each pulse group comprising at least two laser radiation pulses, and the apparatus being arranged to direct the laser radiation pulses of a pulse group at substantially the same processing site of the material, but to direct the laser radiation pulses of successive pulse groups at substantially different processing sites of the material.

According to the invention it is provided that the time interval between two successive laser radiation pulses of a pulse group is in the nanosecond range, in particular in the lower nanosecond range. Studies have shown that, in particular in transparent biological materials and, here again, in particular in corneal tissue, comparatively long-lasting conditions, which enable highly effective injection of a following fs pulse into the material at the desired site, can be created using a fs prepulse suitably adjusted with regard to energy and/or intensity. In this context "long-lasting" means a period which is substantially longer than the interval taught in DE 101 25 206 B4 of, at most, single-digit picoseconds between prepulse and main pulse.

In fact, it has been shown, for example, that micro-changes can be generated with a suitable prepulse in the corneal tissue which can last for up to 10 ns or even beyond. The pulses of a pulse group in the pulse train emitted by the apparatus according to the invention may therefore be spaced correspondingly "far" apart. The advantage thereof is that successive pulses with a time interval in the nanosecond range can be generated with commercially available optical and optoelectronic components stably and with uniform properties more easily than pulses with a time interval of not more than a few picoseconds. This applies both to the pulses themselves and to the time interval between the pulses. The better reproducibility then necessarily leads to better material processing results. In the context of the invention the term "nanosecond range" should not be interpreted so narrowly as to exclude three-digit picoseconds at the outset. On the contrary, in particular high three-digit picosecond intervals between successive pulses of a pulse group should also be seen as lying within the scope of the invention. The micro-changes which may be caused in the corneal material by a prepulse may be present, for example, in the form of micro-damage to the corneal tissue and/or in the form of an increased quantity of free electrons. Such electrons released by the prepulse may, upon impingement of a following main pulse, lead to a more rapid and/or more effective avalanche process, which finally causes the photodisruption.

According to a preferred embodiment, the time interval between successive laser radiation pulses of a pulse group may be less than 100 ns, preferably less than 50 ns and most preferably less than 20 ns. For example, this time interval may lie within the single-digit nanosecond range up to not more than approximately 10 ns.

The preceding pulse of two successive laser radiation pulses of a pulse group preferably has lower energy and/or lower maximum intensity than the following pulse. In this case the energy and/or the maximum intensity of the preceding pulse preferably is not more than half, better not more than a quarter and even better not more than one-tenth of the energy or maximum intensity of the following pulse. For example, the energy or maximum intensity of the preceding pulse may be approximately one-twentieth of that of the following pulse.

According to one embodiment, each pulse group may comprise a total of two laser radiation pulses. However, in the context of the invention, is not ruled out that the pulse groups comprise three or more laser radiation pulses in each case. The inventive nanoscale time interval between successive pulses of a pulse group may be prescribed for only some of the adjacent pulse pairs of a pulse group or for all adjacent pulse pairs of the pulse group. If a pulse group contains three or more pulses, all the pulses of the group may have different energy and/or maximum intensity. In particular, the energy and/or maximum intensity may become increasingly larger from the first to the last pulse of the group. Alternatively, it is possible that some of the pulses of a group, in particular at the end of the group, have approximately the same energy and/or maximum intensity.

The processing apparatus may include a beam deflection device (scanner) by means of which the laser beam can be moved across an area of the material to be processed. In general, the objective will be at to harmonise the deflection speed of the scanner and the time intervals between the pulses of a pulse group and between the groups to one another in such a way that the pulses of a group irradiate substantially the same site but that successive pulse groups irradiate substantially different sites. In this regard it is recommended that the time interval between two successive pulse groups be set at least one order of magnitude, preferably several orders of magnitude, greater than the time interval between successive laser radiation pulses of a pulse group.

As mentioned above, there are commercially available femtosecond lasers the laser oscillator of which can generate laser radiation pulses with a repetition rate in the MHz range, that is, with time intervals in the range of nanoseconds. Also already known are femtosecond lasers which can select, by means of an electro-optical switch, for example, a Pockels cell, individual pulses from the continuous pulse sequence generated by the oscillator, and emit only the selected pulses, generally after amplification, as processing radiation. Such an electro-optical switch yields the advantageous possibility of selecting, by means of the switch, one pulse from the pulses generated by the laser oscillator for each laser radiation pulse of the pulse train emitted. This means that it is not necessary to generate, in a complex, costly and poorly controllable manner, a double pulse from a single pulse in order to form the pulses of a pulse group. Instead, all the pulses of a group, and therefore of the whole train, can be obtained by individual selection from the pulse sequence of the laser oscillator, that is, each emitted treatment pulse corresponds to one laser pulse of the oscillator. If the pulse repetition rate of the laser oscillator used is so high that the time interval between successive pulses of the oscillator is in the range of nanoseconds, in particular in the lower nanosecond range, two successive pulses of the oscillator automatically have the time interval required according to the invention for two successive pulses of a pulse group. The concept of obtaining all the pulses of a pulse group by individual selection from the pulse sequence of a suitably high-frequency fs laser oscillator is regarded as protectable in its own right.

To generate pulses of different intensity in the train, intensity modulation means may be provided which permit setting of a desired intensity for each selected pulse. It is especially advantageous in this case that an electro-optical switch, such as the Pockels cell mentioned, which is also usable for pulse selection, can be used as the intensity modulator. Depending on the desired pulse intensity, the switch is then opened to a greater or lesser degree. It is self-evident that, if required, separate components may be provided for pulse selection and pulse shaping.

The invention can not only be implemented in an apparatus but also has a method aspect. In this regard reference is made to claims 9 to 16.

The invention is further explained below with reference to the attached drawings, in which.

Figure 1:
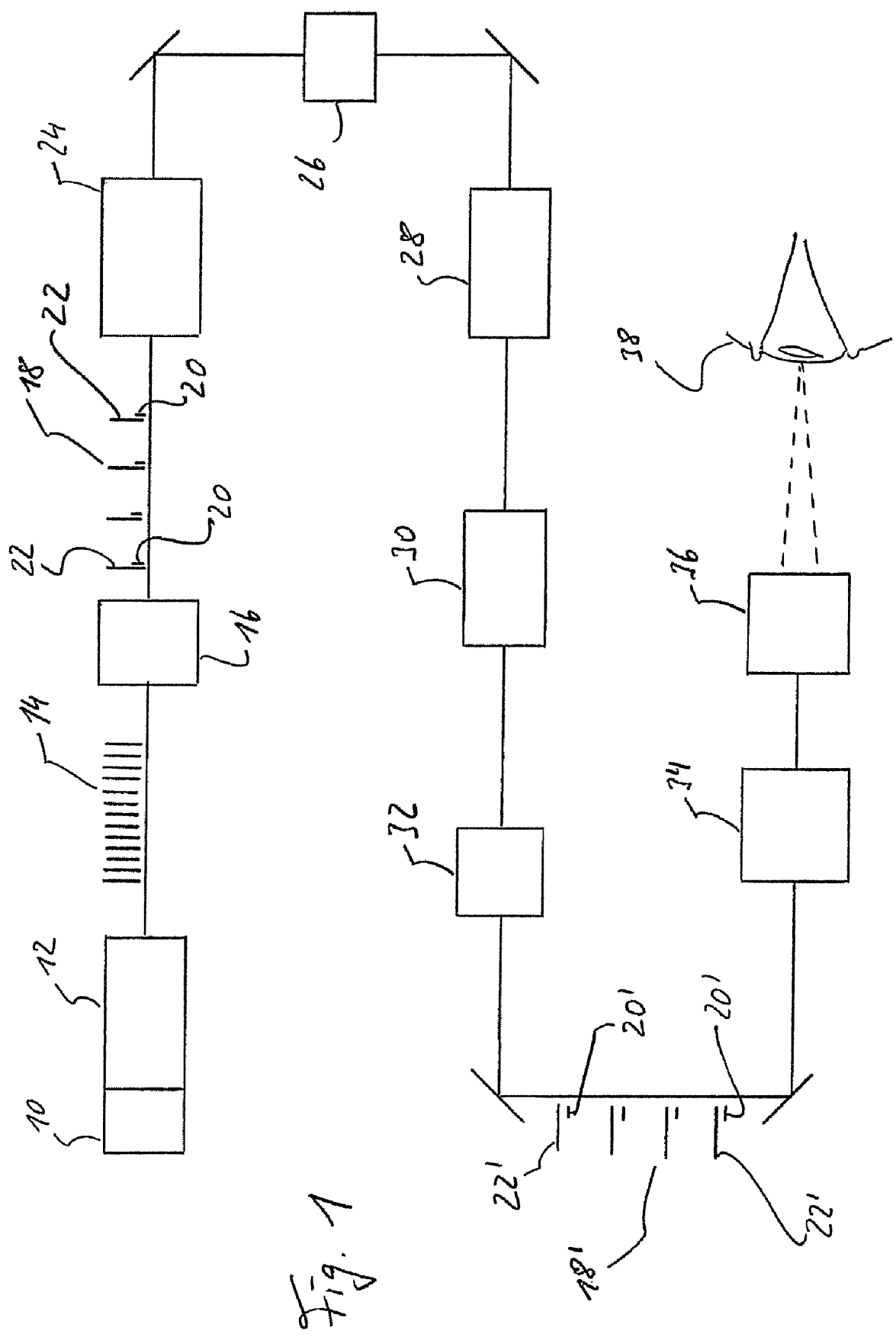
FIG. 1 shows schematically an embodiment of an apparatus for refractive laser-surgical processing of the eye.

Reference is first made to FIG. 1. The laser processing apparatus represented schematically in this Figure comprises a laser oscillator 12, pumped by a pump laser module 10, which generates a sequence of laser radiation pulses which follow one another at regular intervals. The pulse sequence is denoted schematically by reference 14. The duration of the individual pulses is in the femtosecond range, for example, approximately 200 fs. The pulse repetition rate of the laser oscillator 12 is in the MHz range, in particular in the three-digit MHz range, yielding an interval between the pulses of the sequence 14 of approximately 10 ns or even lower. Fs laser oscillators with pulse repetition rates of 100 MHz, 200 MHz or even higher are commercially available as such. The wavelength of the laser radiation generated is, for example, in the lower infrared range, for example between 1000 and 1100 µm. However, other wavelengths, in particular wavelengths in the UV range, are equally possible within the scope of the invention.

From the pulse sequence 14 generated by the laser oscillator 12, a pulse selector 16 selects by individual pulse selection a pulse train, indicated schematically by reference 18, which is composed of successive pulse groups each comprising a lower-energy or lower-intensity preceding pulse 20 and a higher-energy or higher-intensity following pulse 22. Each of the pulses 20, 22 is selected by individual selection of a respective pulse of the sequence 14. The time interval between the pulses 20, 22 of a pulse group corresponds to the time interval between the pulses of the sequence 14, that is, the pulses 20, 22 of a pulse group are formed by selection of two directly successive pulses of the sequence 14. Given the pulse repetition rates of the laser oscillator 12 mentioned as an example earlier, the time interval between the pulses 20, 22 of a pulse group is therefore approximately 10 ns or less. It is self-evident that the pulses of a pulse group do not need in principle to be derived from directly successive pulses of the sequence 14. Rather, it is also possible that the pulse selector 16 selects for a pulse group pulses of the sequence 14 which are separated by at least one intervening pulse.

By contrast, the time interval between the pulse groups of the pulse train 18 is a multiple of the time interval between the pulses 20, 22 of a group. For example, the time interval between the pulse groups may lie in the microsecond range.

It is self-evident that in a modified embodiment each pulse group may contain more than two individual pulses, for example, three.

The pulse selector 16 is in the form of an electro-optical switch which can select individual pulses with adjustable intensity from the pulse sequence 14 generated. Depending on the degree to which the electro-optical switch is "open", the selected pulses are more are less attenuated in terms of intensity. The pulse train 18 represented in FIG. 1 can therefore be produced by appropriate activation of the pulse selector 16. As the electro-optical switch, the pulse selector 16 may contain, for example, a Pockels cell. With a Pockels cell the degree of attenuation of the selected pulses (that is, substantially no attenuation in the cases of the pulses 22 but significant attenuation in the case of the pulses 20) can be determined via the level of the voltage applied.

The selected pulses 20, 22 may then be pre-amplified in an optional pre-amplifier 24 before they undergo their main amplification by means of chirped pulse amplification. In this CPA amplification the pulses 20, 22 are stretched in a time-reversible manner and amplified to a moderate or final energy level. The pulse stretching, which takes place in a stretcher 26, is effected by means of a dispersive element which utilises the different transit times of different spectral pulse components as they pass through the dispersive element in order to expand the pulse. Through the pulse expansion the intensity level of the pulses is reduced, so that, during amplification in a fs main amplifier 28, parasitic non-linear effects can be avoided. The main amplifier 28 may be, for example, a regenerative amplifier.

The amplified pulses available at the output of the main amplifier 28 may be post-amplified in an optional post-amplifier 30 before being recompressed by means of a compressor 32. The compressor 32 compensates, completely in the ideal case, the pulse stretching effected by the stretcher 26 by using a dispersive element with inverse transit time effects. The main amplifier 28 may contain a further pulse selection unit (not indicated separately in FIG. 1) which again selects the amplified pulses, for example, using the so-called cavity dump method, thereby delimiting them more sharply from the background. The post-amplifier 30 may contain a telescopic arrangement for beam divergence.

In readiness at the output of the compressor 32 is a pulse train 18' which corresponds to the pattern of the pulse train 18, but the pulses 20', 22' of which are in total stronger in terms of energy and intensity than the pulses 20, 22 of the pulse train 18. The energy and intensity ratio between the pulses 20' and the pulses 22' preferably corresponds substantially to that between the pulses 20 and 22. This ratio may be, for example, in the range around the value 10, that is, the energy and intensity of the pulses 22' is higher by approximately this value than the energy and intensity of the pulses 20'. The pulse length of the pulses 20', 22' also preferably corresponds substantially to that of the pulses 20, 22. Because completely ideal compensation of the dispersion of the stretcher 26 generally cannot be achieved by the compressor 32, it may be that the pulses 20', 22' have a somewhat longer duration than the pulses 20, 22. In any case, however, the pulse duration of the pulses 20', 22' is also in the femtosecond range, in order to make possible the desired practically athermal material processing with minimal lateral damage.

The pulses 20', 22' are then directed by means of a deflection unit 34 and a focusing unit 36 on to the target area to be processed (here the cornea of a human eye 38). The deflector unit 34 causes deflection of the laser radiation incident on the cornea such that pulses 20', 22' belonging to the same pulse group impinge on substantially the same site on or within the cornea, while the pulses of successive pulse groups impinge on substantially adjacent sites. The lower-energy prepulse 20' of a pulse group causes through multiphoton ionisation the formation of a microplasma at the target point in the cornea. The following higher-energy main pulse 22' can be efficiently injected into this plasma—or, generally, into the material volume modified by the prepulse—and can make possible effective photo-dissection of the stromal tissue. Because of the micro-changes to the corneal material already present, only a comparatively small proportion of the main pulse 22', if anything at all, is transmitted through the focus and reaches the retina. However, the part of the prepulse 20' passing through the focus up to the formation of the micro-change in the material is comparatively small, for which reason the radiation stress on the retina can be substantially reduced as compared to conventional cornea processing methods with single-pulse irradiation. The energy of the main pulses 22' may be, for example, in the single-digit µJ range up to 10 µJ or even above. By contrast, the energy of the pre-pulses 20'—as already indicated above—is, for example, only approximately one-tenth of this energy.

To give a numerical computation purely as an example, it will be assumed that the time interval between the pulses of a pulse group irradiated on the target area is 10 ns, that the interval between pulse groups (that is, the time interval between two successive pulse groups) is 5 µs and the deflection speed of the scanner is 1 m/s. With these numerical values the successive pulse groups impinge on the target area with a spatial interval of 5 µm, while the spatial difference between two successive pulses of a pulse group is only 0.01 µm. The spatial distance between the pulses of a pulse group is therefore smaller by orders of magnitude than the spatial distance between two successive pulse groups, the pulses of a pulse group impinging on substantially the same site. This ensures that the main pulse of a pulse group can actually impinge on the material volume modified by a prepulse of the same pulse group.

Figure 2:
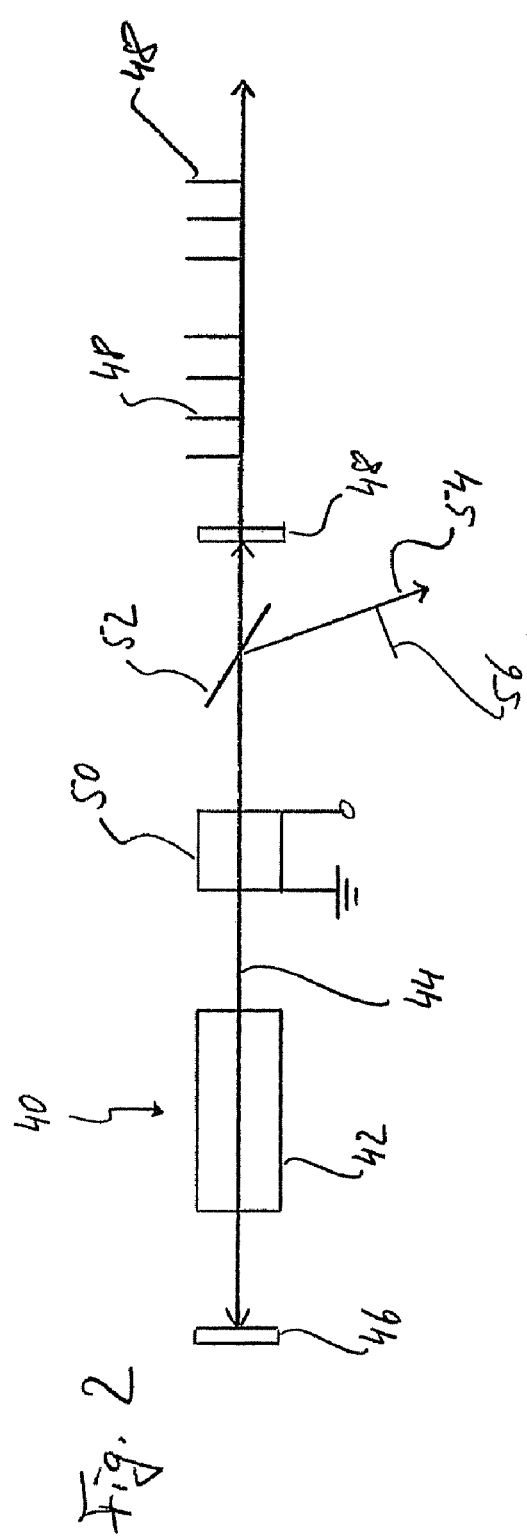
FIG. 2 shows schematically an arrangement for selection of individual pulses from a regular sequence of laser radiation pulses.

Reference is now made to FIG. 2. This Figure shows an exemplary configuration which allows individual pulses to be coupled out from the pulses generated by a laser resonator by means of an electro-optical switch. In FIG. 2 the laser resonator is denoted in general by reference 40. It comprises in a manner known per sea laser medium 42 at each side of which (in relation to the longitudinal resonator axis denoted by 44) are arranged a highly reflecting end mirror 46 and a partially transmitting mirror 48. In addition, an electro-optical switch 50, for example, a Pockels cell, and a polarisation filter 52 formed, for example, by a thin-film polariser, are arranged inside the resonator delimited between the two mirrors 46, 48. By means of a voltage pulse applied to the electro-optical switch 50, the polarisation of a fs pulse circulating in the resonator can be rotated in such a way that the polarisation-rotated pulse is reflected at the polarisation filter 52 and is coupled out of the resonator in a coupling-out direction 54. Such a coupled-out individual pulse is shown as an example at 56. At the times when the electro-optical switch is without voltage the pulses circulating in the resonator are not subjected to polarisation rotation, for which reason they pass through the polarisation filter 52 and are coupled out at the partially transmitting mirror 48. Examples of such pulses coupled out along the main resonator axis 44 are shown at 58. It can be seen that the pulse sequence formed by the pulses 48 has a gap at the position where the polarisation-rotated pulse 56 has been coupled out by the polarisation filter 52.

With the arrangement according to FIG. 2, therefore, a single pulse can be coupled out of the pulse sequence generated by the laser oscillator 40 by controlling the voltage applied to the electro-optical switch 50. Assuming a switching speed of the electro-optical switch 50 in the region of approximately 1 ns, this switching speed is sufficiently fast to be able to select individual pulses in a specified manner with a pulse repetition rate of the oscillator 40 of approximately 10 ns.

Of course, FIG. 2 represents only one of several possible configurations for forming the pulse train 18 of FIG. 1. It is self-evident that, in a modification of the exemplary configuration of FIG. 2, all the pulses circulating in the oscillator as a continuous sequence of pulses of substantially equal intensity can initially be coupled out and individual pulses can only then be coupled out therefrom by means of an electro-optical switch arranged outside the oscillator. This corresponds substantially to the configuration according to FIG. 1, where the pulse selector 16 is shown outside the oscillator 12.

Figure 3:
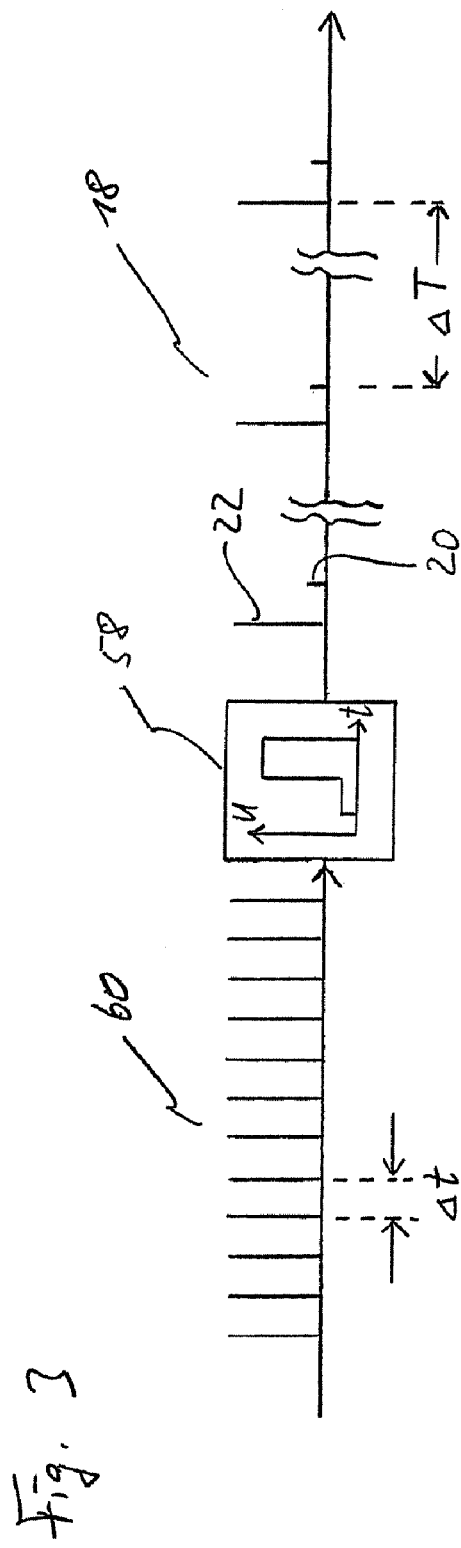
FIG. 3 is a representation to clarify the principle of individual pulse selection and pulse shaping by means of an electro-optical switch.

FIG. 3 clarifies the way in which the pulse train 18 according to FIG. 1 can be formed from a continuous pulse sequence 60 by varying the voltage U applied to a Pockels cell 58 or another electro-optical switch. In FIG. 3, $\Delta t$ denotes the time interval between successive pulses of the sequence 60, that is, the inverted pulse repetition rate, while $\Delta T$ denotes the time interval between successive pulse groups of the pulse train 18. As shown in the U(t) characteristic diagram (t denotes time) contained in the block diagram symbol for the Pockels cell 58, a pulse group comprising a lower-energy prepulse and a higher-energy main pulse can be formed with a stepped curve of the applied voltage U. If a pulse of the sequence 60 reaches the Pockels cell 58 during the lower-voltage stage, this pulse is selected as a prepulse 20, the intensity of which corresponds to the value of the voltage U during the lower-voltage stage. If, however, a pulse of the sequence 60 reaches the cell 58 during the higher-voltage stage, this pulse is allowed to pass through as a main pulse 22, substantially no attenuation of its intensity preferably being caused by the cell 58. At all other times the voltage applied to the Pockels cell 58 is zero. Consequently, none of the pulses of the sequence 60 is transmitted through the cell 58 during these times.

Self-evidently, with more than two pulses per pulse group an appropriately modified voltage characteristic can be used. In particular, a three- or multi-step curve may be used if not only two intensity steps are to be present within a pulse group, but three or more.

The Pockels cell 58 of FIG. 3 may be implemented in the pulse selector 16 of FIG. 1, or may form the electro-optical switch 50 of FIG. 2.

The aim with each pulse group is to achieve material processing in the sense of non-thermal ablation (removal) of material. For single-pulse irradiation, information on the intensity threshold can be found in the prior art, above which threshold, in the statistical mean, non-thermal ablation, or more precisely laser-induced optical breakdown, takes place. The reference to the statistical mean makes it clear that in the case of the thresholds specified in the prior art, not every single pulse needs to lead to optical breakdown. Usually, the thresholds stated in the prior art indicate a value at which approximately 50 percent of the irradiated individual pulses lead to optical breakdown. U.S. Pat. No. 5,656,186, for example, specifies a threshold for optical breakdown with single pulses of $0.2$ $J/cm^2$ to $0.6$ $J/cm^2$, in the case of fs pulses. By contrast, U.S. Pat. No. 5,984,916 specifies, for example, a threshold of $0.2$ $J/cm^2$ to $5$ $J/cm^2$. In both the documents mentioned the thresholds indicated refer to corneal tissue.

In the case of the invention, the following specifications for the intensity of the individual pulses of each pulse group, in comparison to a single pulse threshold applicable to the material concerned, have proved favourable and promising of success. The intensity of a main pulse of a pulse group may be preferably 10 to 300 percent of the single pulse threshold for optical breakdown of the material concerned, while a prepulse preferably has an intensity of 0.1 to 20 percent of the main pulse. If a pulse group consists, for example, of two to ten prepulses and one to two main pulses, the intensity of each main pulse may be close to the threshold stated, for example, approximately 80 to 120 percent. This shows that not every main pulse must necessarily be above the ablation threshold (better: above the threshold for laser-induced optical breakdown), but can very well be below it. This can even be true for a pulse group with a single main pulse. In all cases the prepulse or prepulses will each be below the single-pulse processing threshold. In particular, initiation of an electron avalanche through multiphoton ionisation is aimed at with the prepulses in order to make possible efficient absorption of a main pulse following at a time interval of picoseconds or nanoseconds. In particular, corneal tissue can be processed especially efficiently in this way, and possibly harmful energy irradiation into deeper regions of the eye, in particular the retina, can be effectively avoided.

The invention claimed is:

1. Apparatus for laser processing of a biological material, the apparatus comprising:
   a laser source arranged to emit in the direction of the biological material a train of laser radiation pulses having a pulse duration in the femtosecond range, the pulse train comprising a multiplicity of successive pulse groups, each pulse group of the multiplicity of successive pulse groups comprising at least two laser radiation pulses, wherein a first pulse of two successive laser radiation pulses of a pulse group has a lower energy than a second pulse of the two successive laser radiation pulses of the pulse group, and
   the laser source arranged to direct the laser radiation pulses of each pulse group of the multiplicity of pulse groups at substantially the same processing site of the material, but to direct the laser radiation pulses of successive pulse groups of the multiplicity of pulse groups at substantially different processing sites of the material, the time interval between two successive laser radiation pulses of each pulse group of the multiplicity of pulse groups being in the nanosecond range.

2. Apparatus according to claim 1, wherein the time interval between successive laser radiation pulses of each pulse group of the multiplicity of pulse groups is less than 100 ns.

3. Apparatus according to claim 2, wherein the time interval between successive laser radiation pulses of each pulse group of the multiplicity of pulse groups is less than 10 ns.

4. Apparatus according to claim 2, wherein the time interval between successive laser radiation pulses of each pulse group of the multiplicity of pulse groups is less than 10 ns.

5. Apparatus according to claim 1, wherein the energy of the first pulse is less than half of the energy of the second pulse.

6. Apparatus according to claim 1, wherein each pulse group of the multiplicity of successive pulse groups comprises a total of two laser radiation pulses.

7. Apparatus according to claim 1, wherein the time interval between two successive pulse groups is greater by at least one order of magnitude than the time interval between successive laser radiation pulses of a pulse group.

8. Apparatus according to claim I, wherein the laser source includes a laser oscillator for generating laser radiation pulses at equal time intervals, the laser source being arranged to select, an electro-optical switch, individual pulses from the pulses generated at equal time intervals to be emitted from the laser source as the train of radiation pulses.

9. Apparatus according to claim 8, wherein the laser source further includes an intensity modulation means for setting a desired intensity of a selected pulse and/or of a desired intensity profile within a selected pulse group.

10. Method for laser processing of a biological material, in which method a train of laser radiation pulses having a femtosecond pulse duration is emitted in the direction of the material, the pulse train comprising a multiplicity of successive pulse groups, each pulse group comprising at least two laser radiation pulses, and in which method the laser radiation pulses of a pulse group are further directed at substantially the same processing site of the material but the laser radiation pulses of successive pulse groups are directed at substantially different processing sites of the material, the time interval between two successive laser radiation pulses of a pulse group being in the nanosecond range.

11. Method according to claim 10, wherein two successive laser radiation pulses of a pulse group are emitted with a time interval which is less than 20 ns.

12. Method according to claim 10, wherein a preceding pulse of two successive laser radiation pulses of a pulse group has lower energy than the following pulse.

13. Method according to claim 12, wherein the energy of the preceding pulse is less than one-quarter of the energy of the following pulse.

14. Method according to claim 10, wherein each pulse group comprises a total of two laser radiation pulses.

15. Method according to claim 10, wherein two successive pulse groups are emitted with a time interval which is greater by at least one order of magnitude than the time interval between successive laser radiation pulses of a pulse group.

16. Method according to claim 10, wherein one pulse is selected by electro-optical switching for each laser radiation pulse of the pulse train from a sequence of pulses generated by a laser oscillator at equal time intervals.

17. Method according to claim 16, wherein the intensity of the selected pulses is modulated that at least some of the selected pulses have different pulse intensity.

* * * * *